(12) United States Patent
Roop

(10) Patent No.: US 10,537,421 B2
(45) Date of Patent: Jan. 21, 2020

(54) DIFFRACTIVE-REFRACTIVE LENS

(71) Applicant: Prakhyat Roop, Meerut (IN)

(72) Inventor: Prakhyat Roop, Meerut (IN)

( * ) Notice: Subject to any disclaimer, the term of this patent is extended or adjusted under 35 U.S.C. 154(b) by 0 days.

(21) Appl. No.: 15/535,065

(22) PCT Filed: Aug. 13, 2015

(86) PCT No.: PCT/IB2015/056160
§ 371 (c)(1),
(2) Date: Jun. 12, 2017

(87) PCT Pub. No.: WO2016/166583
PCT Pub. Date: Oct. 20, 2016

(65) Prior Publication Data
US 2018/0021126 A1  Jan. 25, 2018

(30) Foreign Application Priority Data
Apr. 17, 2015 (IN) .................... 1075/2015

(51) Int. Cl.
*A61F 2/16* (2006.01)
*G02B 3/10* (2006.01)
*G02C 7/04* (2006.01)
*G02B 3/08* (2006.01)
*G02B 5/18* (2006.01)

(52) U.S. Cl.
CPC .......... *A61F 2/1618* (2013.01); *A61F 2/1656* (2013.01); *G02B 3/08* (2013.01); *G02B 3/10* (2013.01); *G02B 5/1866* (2013.01); *G02C 7/044* (2013.01); *A61F 2230/0086* (2013.01); *G02C 2202/12* (2013.01); *G02C 2202/20* (2013.01)

(58) Field of Classification Search
CPC ....... A61F 2/1618; A61F 2/1656; G02B 3/08; G02B 3/10; G02C 2202/20
See application file for complete search history.

(56) References Cited

U.S. PATENT DOCUMENTS

| | | | | |
|---|---|---|---|---|
| 5,089,023 | A * | 2/1992 | Swanson | A61F 2/1618 |
| | | | | 359/565 |
| 5,229,797 | A * | 7/1993 | Futhey | A61F 2/1618 |
| | | | | 351/159.48 |
| 2005/0036105 | A1* | 2/2005 | Perel | G02C 7/042 |
| | | | | 351/159.41 |
| 2010/0097569 | A1* | 4/2010 | Weeber | A61F 2/1618 |
| | | | | 351/159.44 |

FOREIGN PATENT DOCUMENTS

| | | | |
|---|---|---|---|
| FR | 2655841 | * | 6/1991 |
| FR | 2655842 | * | 6/1991 |

* cited by examiner

*Primary Examiner* — David H Willse
*Assistant Examiner* — Tiffany P Shipmon

(57) ABSTRACT

An intraocular lens (100) is provided. The intraocular lens (100) includes an anterior surface (102) and a posterior surface (104). The posterior surface (104) defines a plurality of circular bands (114). Each circular band (114) is offset from its adjacent circular band (114) along a longitudinal axis (106) of the intraocular lens (100), wherein a surface (120) extends along the longitudinal axis (106) between peripheries of adjacent circular bands (114).

6 Claims, 2 Drawing Sheets

SECTION A-A

SECTION A-A

DIFFRACTIVE-REFRACTIVE LENS

BACKGROUND

Unless otherwise indicated herein, the materials described in this section are not prior art to the claims in this application and are not admitted to be prior art by inclusion in this section.

FIELD

The disclosed subject matter in general relates to a diffractive-refractive lens, which may be used for ophthalmic purpose as multifocal contact-lens, spectacle lens, and more particularly as multifocal intraocular lens. It may also be used for non-ophthalmic purposes.

DISCUSSION OF RELATED FIELD

Intraocular lenses (IOLs) are implanted to replace the natural crystalline lens of the human eye. Cataract and vision correction surgeries are the main reason for such replacement surgeries. These IOLs are either monofocal or multifocal in function. Monofocal lenses have the capability of focussing either near or distant objects, whereas multifocal lens have the capability of focusing both near and distant object simultaneously.

Multifocal capability in IOLs is achieved through diffraction grating. However, in most cases the design of diffraction gratings is such that there is considerable loss in image contrast sensitivity because of loss of considerable light energy and also uncontrolled overlap of refractive and diffractive phenomena. Further, the diffraction gratings may even contribute to halos and glares, which are added distractions to the patient with the newly implanted IOL. Such drawbacks of conventional multifocal IOLs delay the process of the patient getting accustomed to the implanted lens and may not give optimal quality of vision at either focus. In light of the foregoing discussion an improved multifocal IOL is desired.

SUMMARY

An embodiment provides an intraocular lens. The intraocular lens includes an anterior surface and a posterior surface. The posterior surface defines a plurality of circular bands. Each circular band is onset from its adjacent circular band along a longitudinal axis of the intraocular lens, wherein a surface extends along the longitudinal axis between peripheries of adjacent circular bands.

BRIEF DESCRIPTION OF DRAWINGS

Embodiments are illustrated by way of example and not limitation in the Figures of the accompanying drawings, in which like references indicate similar elements and in which.

DETAILED DESCRIPTION

Figure 1A:
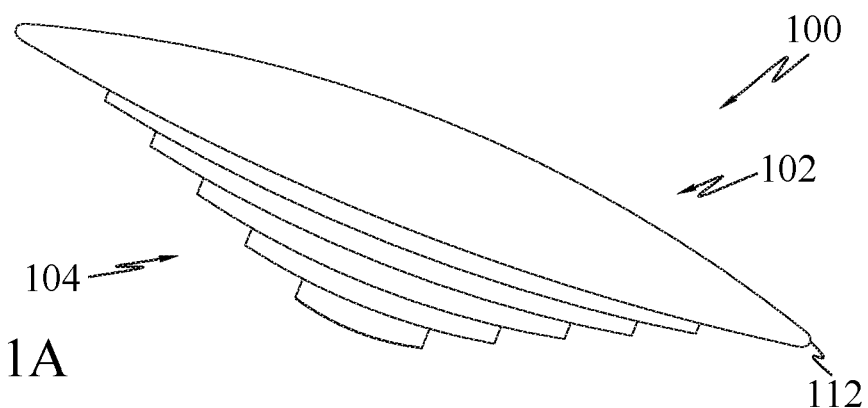
FIG. 1A is a perspective view of an exemplary multifocal intraocular lens 100.
Figure 1B:
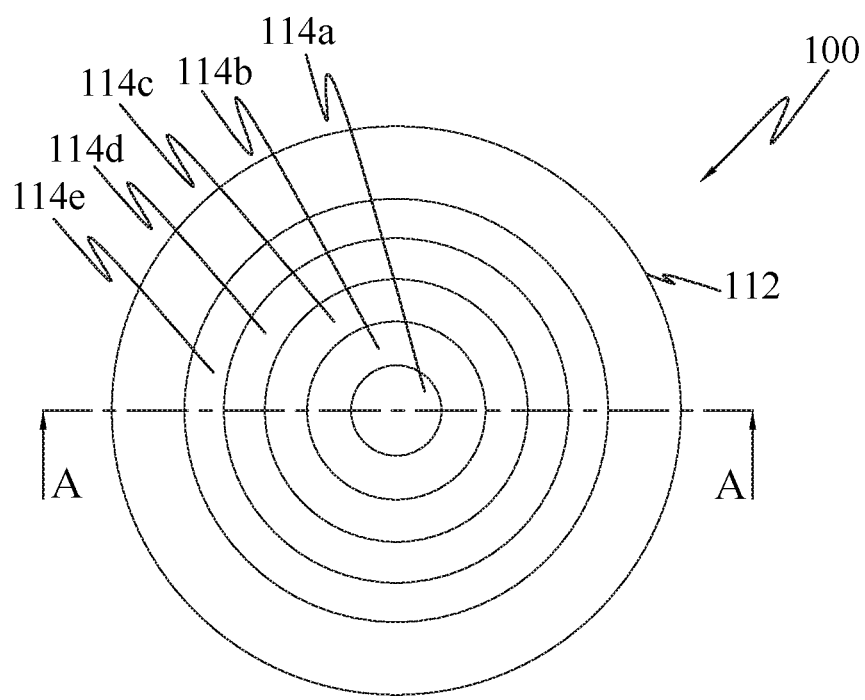
FIG. 1B is a back view of the intraocular lens 100 of FIG. 1A.
Figure 1C:
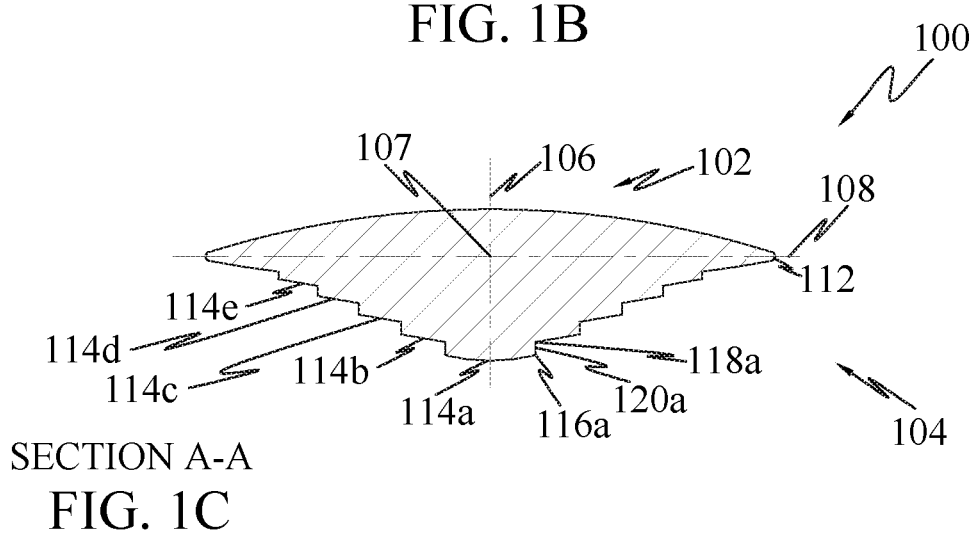
FIG. 1C is a sectional view (A-A) of the intraocular lens 100 of FIG. 1B.
Figure 1D:
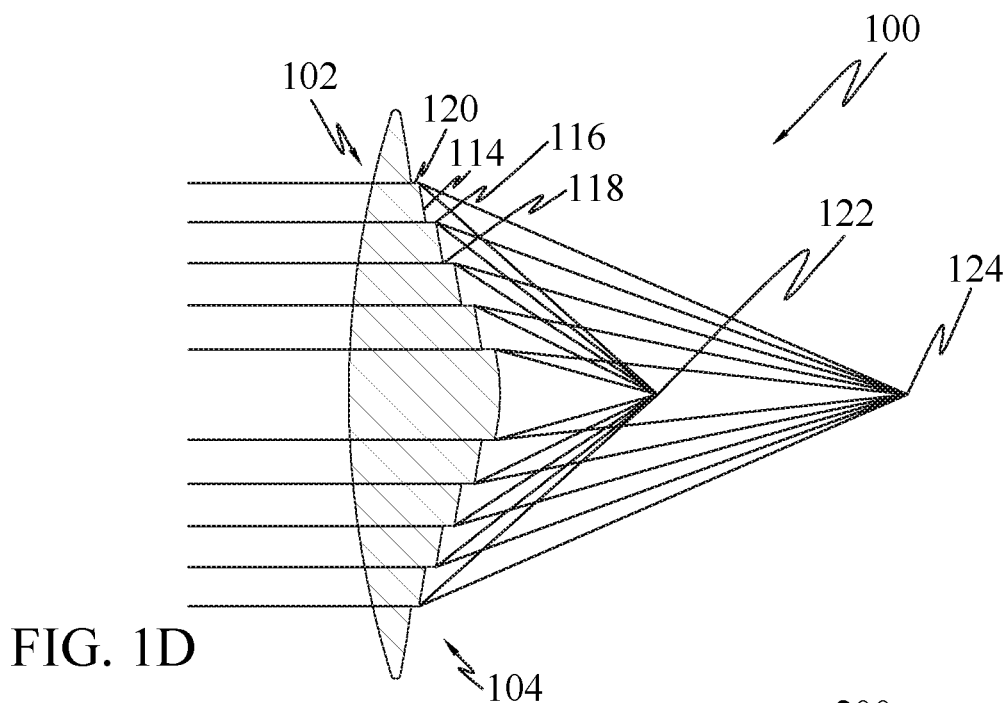
FIG. 1D illustrates simplified exemplary light distribution of the intraocular lens 100 of FIG. 1A.

The following detailed description includes references to the accompanying drawings, which form part of the detailed description. The drawings show illustrations in accordance with example embodiments. These example embodiments are described in enough detail to enable those skilled in the art to practice the present subject matter. However, it will be apparent to one of ordinary skill in the art that the present invention may be practiced without these specific details. In other instances, well-known methods, procedures and components have not been described in detail so as not to unnecessarily obscure aspects of the embodiments. The embodiments can be combined, other embodiments can be utilized or structural and logical changes can be made without departing from the scope of the invention. The following detailed description is, therefore, not to be taken as a limiting sense.

In this document, the terms "a" or "an" are used, as is common in patent documents, to include one or more than one. In this document, the term "or" is used to refer to a nonexclusive "or," such that "A or B" includes "A but not B," "B but not A," and "A and B," unless otherwise indicated.

Now referring to the figures and more specifically to FIGS. 1A-1D, a multifocal intraocular lens 100 may include an anterior surface 102 and a posterior surface 104. The multifocal intraocular lens 100 has a lateral axis 108 and a longitudinal axis 106. The multifocal intraocular lens 100 may have a peripheral limit 112. The anterior surface 102 and the posterior surface 104 may converge to define the peripheral limit 112. However the posterior surface is modified to give added advantage of multifocality without compromising the existent optical properties conferred by the anterior and unmodified posterior surface of corresponding monofocal lens.

The posterior surface 104 may define a plurality of circular bands 114a, 114b, 114c . . . (may be referred to as "circular band 114" or "circular bands 114"). The circular bands 114 are concentric to the longitudinal axis 106. The centre most circular band 114a is smallest in terms of diameter and is longitudinally farthest away from an intersection point 107 of the longitudinal axis 106 and the lateral axis 108. The longitudinal distance between the circular bands 114 and the intersection point 107 decreases with increase in their diameter. In other words, a circular band 114e which has the largest diameter and encircles all the remaining circular bands 114 is longitudinally closest to the intersection point 107. In other words, longitudinal distance between an outer periphery (Ex: outer periphery 116a) of a circular band (Ex: circular band 114a) and the lateral axis 108 of the intraocular lens 100 is longer than longitudinal distance between an inner periphery (Ex: inner periphery 118a) of a circular band (Ex: circular band 114b) surrounding said circular band (Ex: circular band 114a) and the lateral axis 108.

Each circular band 114 is offset from its adjacent circular band 114 along the longitudinal axis 106. A surface extends along the longitudinal axis 106 between peripheries of adjacent circular bands 114.

As an example, the surface 120a (may be referred to as "surface 120") extends between adjacent circular bands 114a and 114b. The surface 120a extends from outer periphery 116a of the circular band 114a and inner periphery 118a of the circular band 114b.

In an embodiment, the surfaces 120 may be perpendicular to the lateral axis 108 (parallel to the longitudinal axis 106) and concentric to the longitudinal axis 106.

In an embodiment, step height of the surfaces 120 may vary as it moves away from the longitudinal axis 106 as a function of the radius of the circular bands 114. These surfaces 120 act as diffractive gratings and splits light on two focal points (near focus 122 and far focus 124) thus giving the lens its multifocal capabilities.

In an embodiment, step height of the surfaces 120 may decrease as it moves away from the longitudinal axis 106.

In another embodiment, posterior surface 104 of each of the circular bands 114 has a radius of curvature corresponding to the basic refractive power of the lens. This eliminates loss of light in between adjacent circular bands. Thus if an exemplary illustration of similar design is taken in which all step heights are reduced to zero it results in a corresponding monofocal lens.

In an embodiment, the radii of curvature of at least two adjacent circular bands 114 are equal.

In an embodiment, the radii of curvature of at least two adjacent circular bands 114 differ from each other.

The multifocal intraocular lens 100 achieves multifocal capability through principles of diffractive grating and refraction. Refraction occurs at the posterior surface 104 of each circular band 114 and it corresponds to distance focus (power) 124 of the lens. The surface 120 between two adjacent circular bands 114 acts as diffraction grating, which diffracts the light rays. Post diffraction, light rays get distributed between the far 124 and near 122 foci. The interference of these diffracted light rays results in multifocality.

Equation 1 is used to determine outer radius of each of the circular bands 114.

$$r_i^2 = r_0^2 + 2i\lambda f \quad \text{(Equation 1)}$$

Wherein,
"i" denotes the number of the circular band (i= 0, 1, 2, 3 . . . ), "0" being the inner most circular band
"$r_i$" denotes the radius of the "$i^{th}$" circular band ($r_0$ may be 250 μm)
"λ" denotes the wavelength of visible light (which can be 550 nm)
"f" denotes the focal length of near focus (3 Dioptre) of the multifocal intraocular lens.
Thus the value of radii of circular bands is determined by the additional near power (add power) desired to be given in a lens, which has been taken as 3 Diopters in this example, however it may vary from 2.5 D to 4.0 D. Value of $r_0$ may vary from 250 micron to 750 micron.
Equation 2 determines the step height of the circular bands $$h_i = \{0.7 + 0.01[i^{(1+0.1i)} - (i-1)]\} * \lambda * f_{apd}/(n_2 - n_1) \quad \text{(Equation 2)}$$

Wherein,
"$h_i$" denotes the height of the surface 120 extending from outer periphery of the "$i^{th}$" circular band
$n_2$ is the refractive index of the lens ($n_2$ may be 1.55)
$n_1$ is the refractive index of the medium surrounding the lens, which in this case is aqueous humor ($n_1$ may be 1.336)
and $f_{apd}$ is determined by equation 3

$$f_{apd} = 1 - (r_i/r_{out})^{(2+0.5i)} \quad \text{(Equation 3)}$$

Wherein,
"$f_{apd}$" denotes function of apodization for each of the circular bands
"$r_{out}$" denotes the radius of the outmost ring which does not have a corresponding surface 120 extending from its outer periphery ($r_{out}$ may be 1834 μm).
By means of apodization the heights of circular band is gradually reduced towards the periphery. In some embodiments the height may be constant i,e there may be no apodization.
Diffraction efficiency of a particular band is determined by equation 4

$$DE = (\sin \pi(\alpha_i - p)/\pi(\alpha - p))^2 \quad \text{(Equation 4)}$$

Wherein,
"DE" denotes diffraction efficiency of the band, which is used to determine the amount of light being focused on the near focus point and the far focus point
p=0 for far and 1 for near $$\alpha_i = h_i * (n_2 - n_1)/\lambda \quad \text{(Equation 5)}$$

Thus it is evident from equation 4 and 5 that height determines the diffraction efficiency of particular band.

Table 1 below provides values of an exemplary multifocal intraocular lens 100 which has nine circular bands with corresponding surfaces 120 of their respective step heights based on the above mentioned equations.

TABLE 1

| Number of circular bands (i) | Radius of circular bands ($r_i$) (μm) | Function of Apodisation ($f_{apd}$) | Height of surface ($h_i$) (microns) | Light distribution (%) (Far:Near) |
|---|---|---|---|---|
| 0 | 250 | 0.98412 | 1.79 | 3:97 |
| 1 | 655 | 0.92358 | 1.68 | 4:96 |
| 2 | 892 | 0.88485 | 1.62 | 7:93 |
| 3 | 1078 | 0.84412 | 1.56 | 11:89 |
| 4 | 1237 | 0.79318 | 1.50 | 20:80 |
| 5 | 1377 | 0.72453 | 1.43 | 28:72 |
| 6 | 1504 | 0.62862 | 1.32 | 44:56 |
| 7 | 1622 | 0.49162 | 1.14 | 70:30 |
| 8 | 1731 | 0.29275 | 0.79 | 96:4 |
| $r_{out}$ | 1834 | 0 | 0 | 0:0 |

Table 2 below provides step height values of surfaces 120 of another exemplary embodiment of multifocal intraocular lens 100 not based upon above mentioned equations. In this example, light distribution of the bands varies linearly. For this example, the desired function of lens in a biological system is determined and required heights are calculated by using equations 1, 2, 4 and 5.

TABLE 2

| Number of circular bands (i) | Height of surface ($h_i$) (microns) | Light distribution (%) (Far:Near) |
|---|---|---|
| 0 | 1.58 | 10:90 |
| 1 | 1.50 | 20:80 |
| 2 | 1.42 | 30:70 |
| 3 | 1.36 | 40:60 |
| 4 | 1.28 | 50:50 |
| 5 | 1.22 | 60:40 |
| 6 | 1.14 | 70:30 |
| 7 | 1.07 | 80:20 |
| 8 | 0.96 | 90:10 |
| $r_{out}$ | 0 | 0:0 |

Figure 2A:
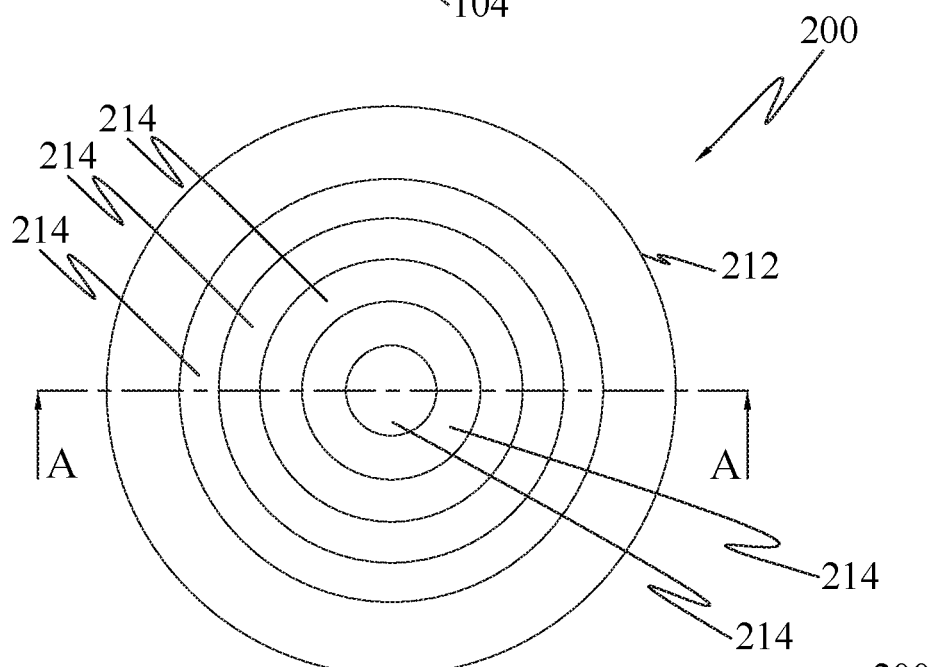
FIG. 2A is a back view of another exemplary intraocular lens 200.
Figure 2B:
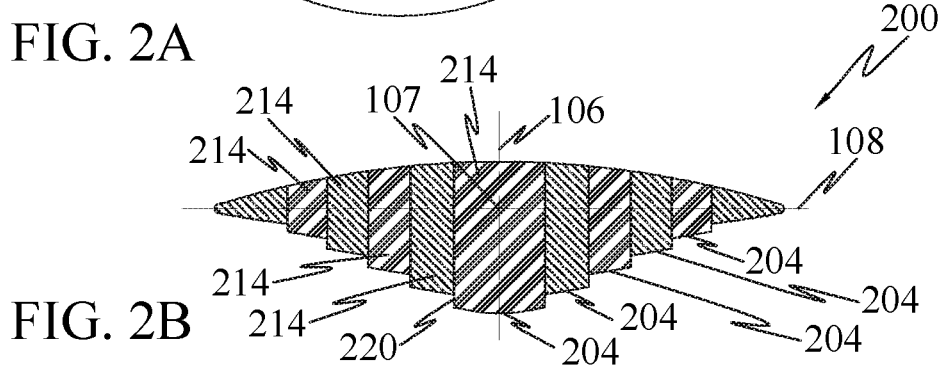
FIG. 2B is a sectional view of another exemplary multifocal intraocular lens 200.

Now referring to FIG. 2A, another embodiment of multifocal intraocular lens 200 which also includes a plurality of circular bands 214 and a periphery 212. Apart from having diffractive gratings, either the refractive index of the material may vary between two adjacent surfaces 220 or the material is same but curvature of circular bands 204 varies between two adjacent surfaces 220. This gives an option of providing additional multifocality based on refractive power in addition to diffraction from gratings.

In another embodiment the number of bands may be reduced or varied according to the utility of the desired lens by omitting some bands of certain orders but still maintaining the relationship of the radius with its order and corresponding height.

In another embodiment there may be two sets of bands having radii relating to two add powers in a single lens.

Although embodiments have been described with reference to specific example embodiments, it will be evident that various modifications and changes may be made to these embodiments without departing from the broader spirit and scope of the system and method described herein. Accordingly, the specification and drawings are to be regarded in an illustrative rather than a restrictive sense.

Many alterations and modifications of the present invention will no doubt become apparent to a person of ordinary skill in the art after having read the foregoing description. It is to be understood that the phraseology or terminology employed herein is for the purpose of description and not of limitation. It is to be understood that the description above contains many specifications, these should not be construed as limiting the scope of the invention but as merely providing illustrations of some of the personally preferred embodiments of this invention. Thus the scope of the invention should be determined by the appended claims and their legal equivalents rather than by the examples given.

What is claimed is:

1. An intraocular lens comprising:
   an anterior surface; and
   a posterior surface defining a plurality of circular bands; wherein,
      each circular band, defined by the posterior surface, is offset from its adjacent circular band along a longitudinal axis of the intraocular lens, wherein a surface extends along the longitudinal axis between peripheries of adjacent circular bands;
      each of the circular bands comprises a curved surface having a radius of curvature, wherein the curved surface is generally parallel to a lateral axis of the intraocular lens to define a stepped configuration of the circular bands and not a serrated configuration; and
      in case of each of the circular bands defined by the posterior surface, longitudinal distance between an outer periphery of a circular band and the lateral axis of the intraocular lens is longer than longitudinal distance between an inner periphery of a circular band surrounding said circular band and the lateral axis, in such a way that, the posterior surface defines a generally inverted pyramid shape relative to the anterior surface, wherein the inverted pyramid comprises a base and a tip portion, wherein the base extends from an outer periphery of the anterior surface and the tip portion is disposed away from the anterior surface.

2. The intraocular lens of claim 1, wherein the radius of curvature of at least two adjacent circular bands are equal.

3. The intraocular lens of claim 1, wherein the radius of curvature of at least two adjacent circular bands differ from each other.

4. The intraocular lens of claim 1, wherein the surfaces extending along the longitudinal axis between peripheries of adjacent circular bands are parallel to the longitudinal axis.

5. The intraocular lens of claim 1, wherein height of the surfaces extending along the longitudinal axis between peripheries of adjacent circular bands decrease as it moves away from the longitudinal axis.

6. The intraocular lens of claim 1, wherein a refractive index of material of at least two surfaces differ from each other.

* * * * *